United States Patent [19]

Mori

[11] Patent Number: 4,991,190

[45] Date of Patent: Feb. 5, 1991

[54] ROTATE-ROTATE TYPE X-RAY COMPUTERIZED TOMOGRAPHIC IMAGING APPARATUS

[75] Inventor: Issei Mori, Nishinasunomachi, Japan

[73] Assignee: Kabushiki Kaisha Toshiba, Kawasaki, Japan

[21] Appl. No.: 391,931

[22] Filed: Aug. 10, 1989

[30] Foreign Application Priority Data

Aug. 15, 1988 [JP] Japan .................. 63-203015

[51] Int. Cl.⁵ .............................. A61B 6/00
[52] U.S. Cl. .............................. 378/9; 378/4; 378/19
[58] Field of Search .................. 378/4, 9, 19

[56] References Cited

U.S. PATENT DOCUMENTS

| | | | |
|---|---|---|---|
| 4,176,279 | 11/1979 | Schwierz et al. | 378/19 |
| 4,196,352 | 4/1980 | Berninger et al. | 378/9 |
| 4,303,830 | 12/1981 | Heinzelmann et al. | 378/9 |
| 4,384,359 | 5/1983 | Franke | 378/9 |
| 4,637,040 | 1/1987 | Sohval et al. | 378/9 |

Primary Examiner—Janice A. Howell
Assistant Examiner—Kim-Kwok Chu
Attorney, Agent, or Firm—Finnegan, Henderson, Farabow, Garrett and Dunner

[57] ABSTRACT

There is provided a rotate-rotate type X-ray computerized tomographic imaging apparatus having a plurality of pairs of mutually facing X-ray sources and multichannel X-ray detectors, wherein a high-resolution scan mode or a high-speed scan mode is selected. The apparatus includes a stationary body, a rotational body arranged rotatably in the stationary body and having an insertion section in which a subject is inserted, a K-number of X-ray sources provided on the rotational body, a K-number of multichannel X-ray detectors movably mounted on the rotational body, data processing means for collecting data from the K-number of multichannel X-ray detectors and for carrying out processing relating to image reconstruction, and control means for performing at least a control of rotation of the rotational body, a control of the data collection, and a control of the processing relating to the data reconstruction.

5 Claims, 7 Drawing Sheets

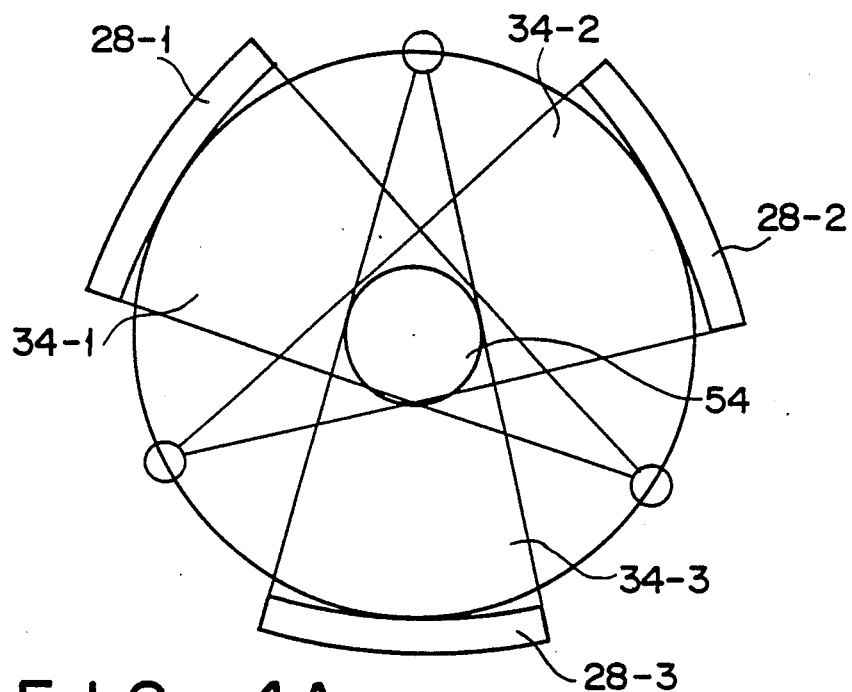
F I G. 4A
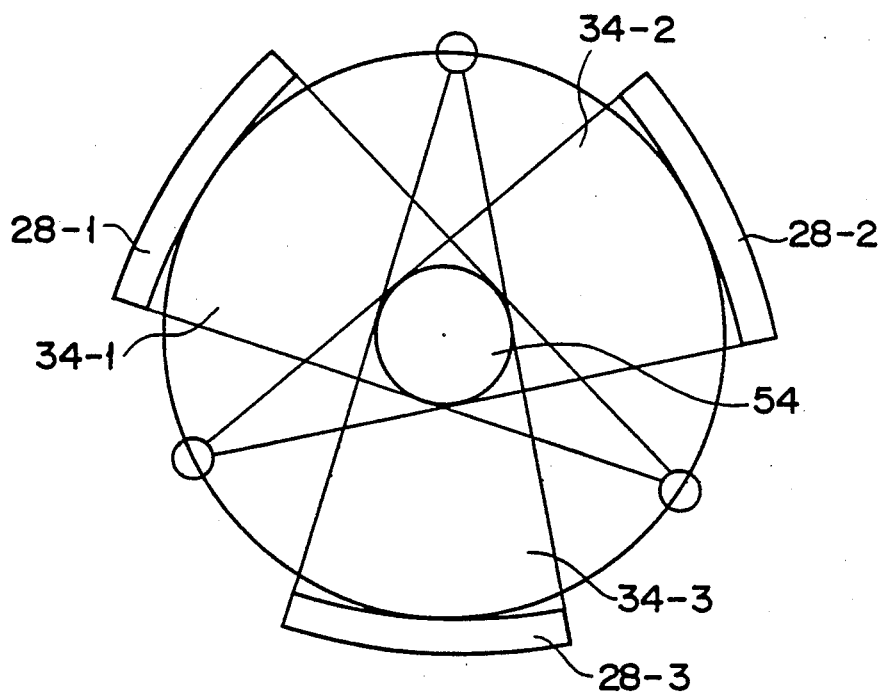
F I G. 4B

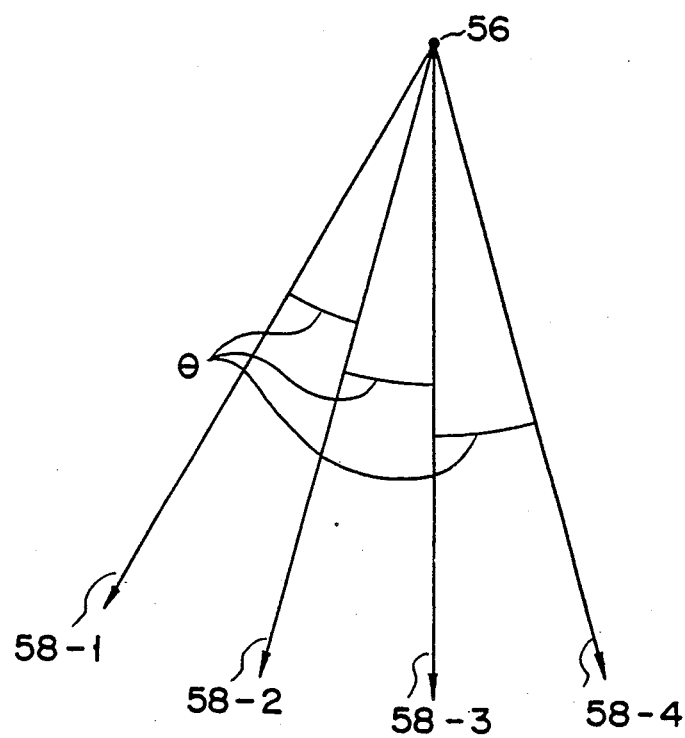
F I G. 5A
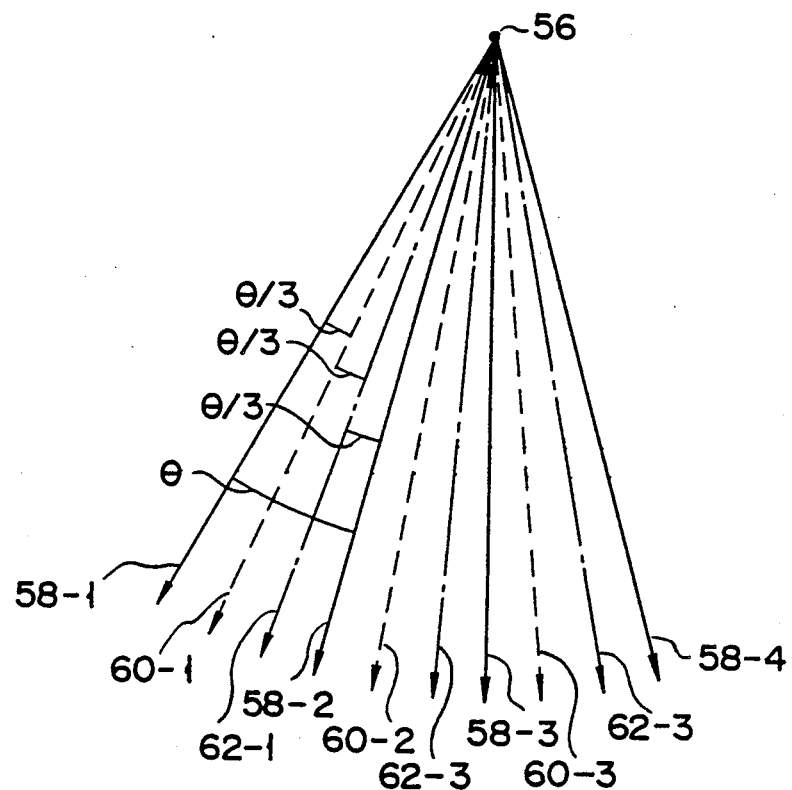
F I G. 5B

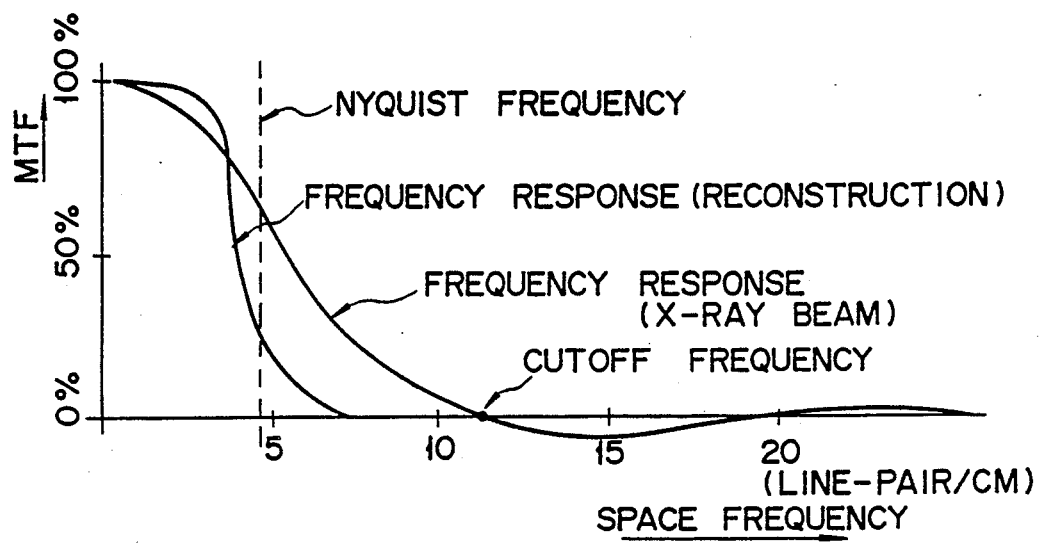
F I G. 6A
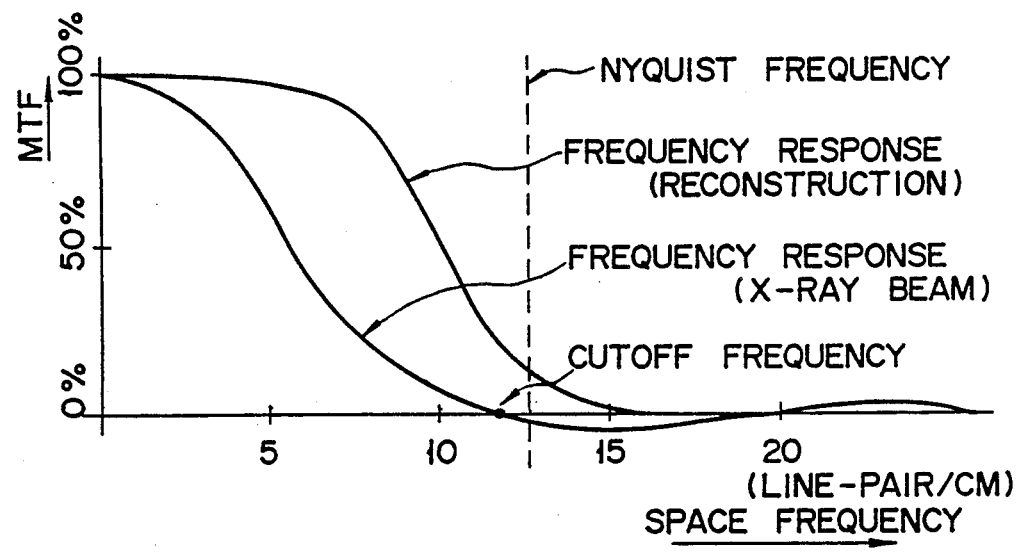
F I G. 6B

ROTATE-ROTATE TYPE X-RAY COMPUTERIZED TOMOGRAPHIC IMAGING APPARATUS

BACKGROUND OF THE INVENTION

1. Field of the Invention

The present invention relates to a rotate-rotate type computerized tomographic imaging apparatus comprising pairs of X-ray sources and multichannel X-ray detectors, each pair of the X-ray source and the multichannel X-ray detector being rotatable in the state wherein the X-ray source and the multichannel X-ray detector face each other.

2. Description of the Related Art

U.S. Pat. No. 4,196,352 and U.S. Pat. No. 4,384,359 disclose apparatuses having pairs of X-ray sources and X-ray detectors. In these documents, three pairs of X-ray sources and X-ray detectors are arranged symmetrical with respect to a rotational body of a gantry.

In an apparatus having three pairs of the X-ray sources and X-ray detectors, data, which is obtainable by rotating a rotational body of a conventional apparatus (having only one pair of an X-ray source and an X-ray detector) by 360°, can be obtained only by rotating the pairs by 120°. Namely, the scan time can be reduced to ⅓, compared to the conventional apparatus. However, despite the fact that the total number of detectors is tripled, the space resolution is not enhanced. This can also be said in the case of the rotation of 240° or 360° of the rotational body of the apparatus. Namely, a line passing through a central point between the X-ray source and each channel represents sampling points. Even if the apparatus is rotated by 120°, 240° or 360°, the positions of the sampling points are unchanged.

SUMMARY OF THE INVENTION

The object of the present invention is to provide a rotate-rotate type X-ray computerized tomographic imaging apparatus which can produce an image of high resolution. This object can be attained by a rotate-rotate type X-ray computerized tomographic imaging apparatus including:

a stationary body;

a rotational body arranged rotatably in the stationary body and having an insertion section in which a subject is inserted;

a K-number of X-ray sources provided on the rotational body;

a K-number of multichannel X-ray detectors movably mounted on the rotational body;

data processing means for collecting data from the K-number of multichannel X-ray detectors and for carrying out processing relating to image reconstruction; and control means for performing at least a control of rotation of the rotational body, a control of the data collection, and a control of the processing relating to the data reconstruction, the apparatus being improved in that:

the K-number of X-ray sources are arranged to face the K-number of multichannel X-ray detectors, respectively, thus constituting a K-number of pairs; and a (K−1)-number of the multichannel X-ray detectors of the pairs are arranged asymmetrical with the corresponding X-ray sources with respect to the rotation axis of the rotational body, such that a data sampling pitch is set to 1/K.

The above object can also be achieved by a rotate-rotate type X-ray computerized tomographic imaging apparatus, including:

a stationary body;

a rotational body arranged rotatably in the stationary body and having an insertion section in which a subject is inserted;

a K-number of X-ray sources movably mounted on the rotational body;

a K-number of multichannel X-ray detectors provided on the rotational body;

data processing means for collecting data from the K-number of multichannel X-ray detectors and for carrying out processing relating to image reconstruction; and control means for performing at least a control of rotation of the rotational body, a control of the data collection, and a control of the processing relating to the data reconstruction, the apparatus being improved in that:

the K-number of X-ray sources are arranged to face the K-number of multichannel X-ray detectors, respectively, thus constituting an K-number of pairs; and a (K-1)-number of the X-ray sources of the pairs are arranged on the rotational body asymmetrically with the corresponding multichannel X-ray detectors with respect to the rotation axis of the rotational body, such that a data sampling pitch is set to 1/K.

The above object can also be achieved by a rotate-rotate type X-ray computerized tomographic imaging apparatus, including:

a stationary body;

a rotational body arranged rotatably in the stationary body and having an insertion section in which a subject is inserted;

a K-number of X-ray sources provided on the rotational body; and a K-number of multichannel X-ray detectors provided on the rotational body, the apparatus being improved in that:

the K-number of X-ray sources are arranged to face the K-number of multichannel X-ray detectors, respectively, thus constituting an K-number of pairs; and the respective pairs are arranged asymmetrical with respect to the rotation axis of the rotational body.

According to the above structures, when data groups of different pairs of X-ray sources and X-ray detectors, which are obtained after one rotation of the frame, are aligned, data having a smaller data pitch than the pitch used in a conventional one-pair type apparatus can be produced. As a result, an image having high space resolution can be obtained. In addition, even if the rotational frame is not rotated over 360°, projection data groups similar to those obtained by a single-pair construction can be produced. Based on these data groups, reconstruction of images is carried out, and the scanning speed is increased, and the scanning time is shortened.

BRIEF DESCRIPTION OF THE DRAWINGS

FIGS. 1 to 3 show a structure of a first embodiment of a rotate-rotate type X-ray computerized tomographic imaging apparatus according to the present invention, wherein FIG. 1 is a front view of a gantry, FIG. 2 is a cross section of a rotational body taken along line II—II in FIG. 1, and FIG. 3 is a block diagram of an electric circuit.

FIGS. 4A and 4B show the states of X-ray paths for different scan modes employed in the first embodiment, wherein FIG. 4A is a diagram showing the state of a high-resolution scan, and FIG. 4B is a diagram showing the state of a high-speed scan.

FIGS. 5A and 5B illustrate the division of sampling pitches employed in the first embodiment, wherein FIG. 5A shows normal sampling pitches, and FIG. 5B shows divided sampling pitches.

FIGS. 6A and 6B show the realization of high resolution in the first embodiment, wherein FIG. 6A shows characteristics representing the relationship between a Nyquist frequency, an MTF (modulation transfer function), and a space frequency when normal sampling pitches are employed, and FIG. 6B shows characteristics representing the relationship between a Nyquist frequency, an MTF (modulation transfer function), and a space frequency when divided sampling pitches are employed.

FIGS. 7 to 9 show a structure of a second embodiment of the rotate-rotate type X-ray computerized tomographic imaging apparatus according to the present invention, wherein FIG. 7 is a front view of a gantry, FIG. 8 is a cross section of a rotational body taken along line VIII—VIII in FIG. 7, and FIG. 9 is a block diagram of an electric circuit.

DETAILED DESCRIPTION OF THE PREFERRED EMBODIMENTS

Figure 1:
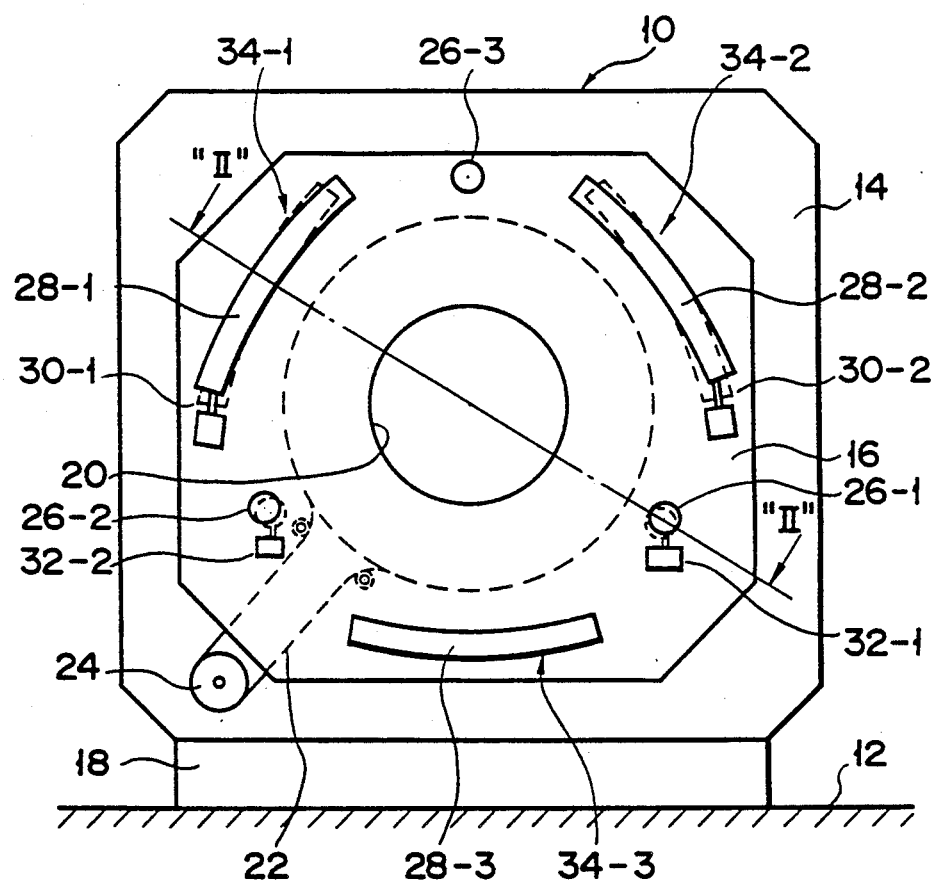
Figure 2:
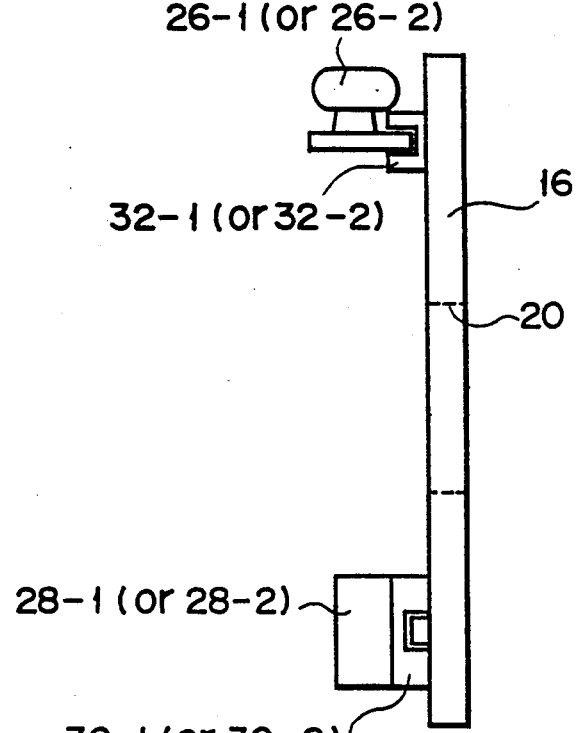

A first embodiment of the rotate-rotate type X-ray computerized tomographic imaging apparatus according to the present invention will now be described with reference to FIGS. 1 to 3.

The main feature of the apparatus according to the first embodiment resides in the structure of a gantry 10. The gantry 10 is placed on a floor 12. In the gantry 10, a rotational frame 16 is rotatably arranged within a stationary frame 14. The stationary frame 14 is provided with a tilting mechanism 18 which serves to tilt the gantry 10 in a direction perpendicular to the face of FIG. 1. An insertion hole 20, into which a subject is inserted, is formed at a central area of the rotational frame 16.

A timing belt 22 is passed over the rotational frame 16. The timing belt 22 is driven by a motor 24 mounted on the stationary frame 14, so that the rotational frame 16 may be rotated.

The rotational frame 16 has three X-ray sources 26-1, 26-2 and 26-3, and three multichannel X-ray detectors 28-1, 28-2 and 28-3. The X-ray sources 26-1 and 26-2 are provided with shift mechanisms 32-1 and 32-2, and the multichannel X-ray detectors 28-1 and 28-2 are provided with shift mechanisms 30-1 and 30-2. The X-ray source 26-1 and the multichannel X-ray detector 28-1 constitute a first pair 34-1, the X-ray source 26-2 and the multichannel detector 28-2 constitute a second pair 34-2, and the X-ray source 26-3 and the multichannel X-ray detector 28-3 constitute a third pair 34-3. The first to third pairs 34-1, 34-2 and 34-3 are symmetrical or asymmetrical with respect to the axis of rotation of the rotational frame 16. The multichannel X-ray detectors 28-1, 28-2 and 28-3 may be of the ion chamber type or solid-state type.

Figure 3:
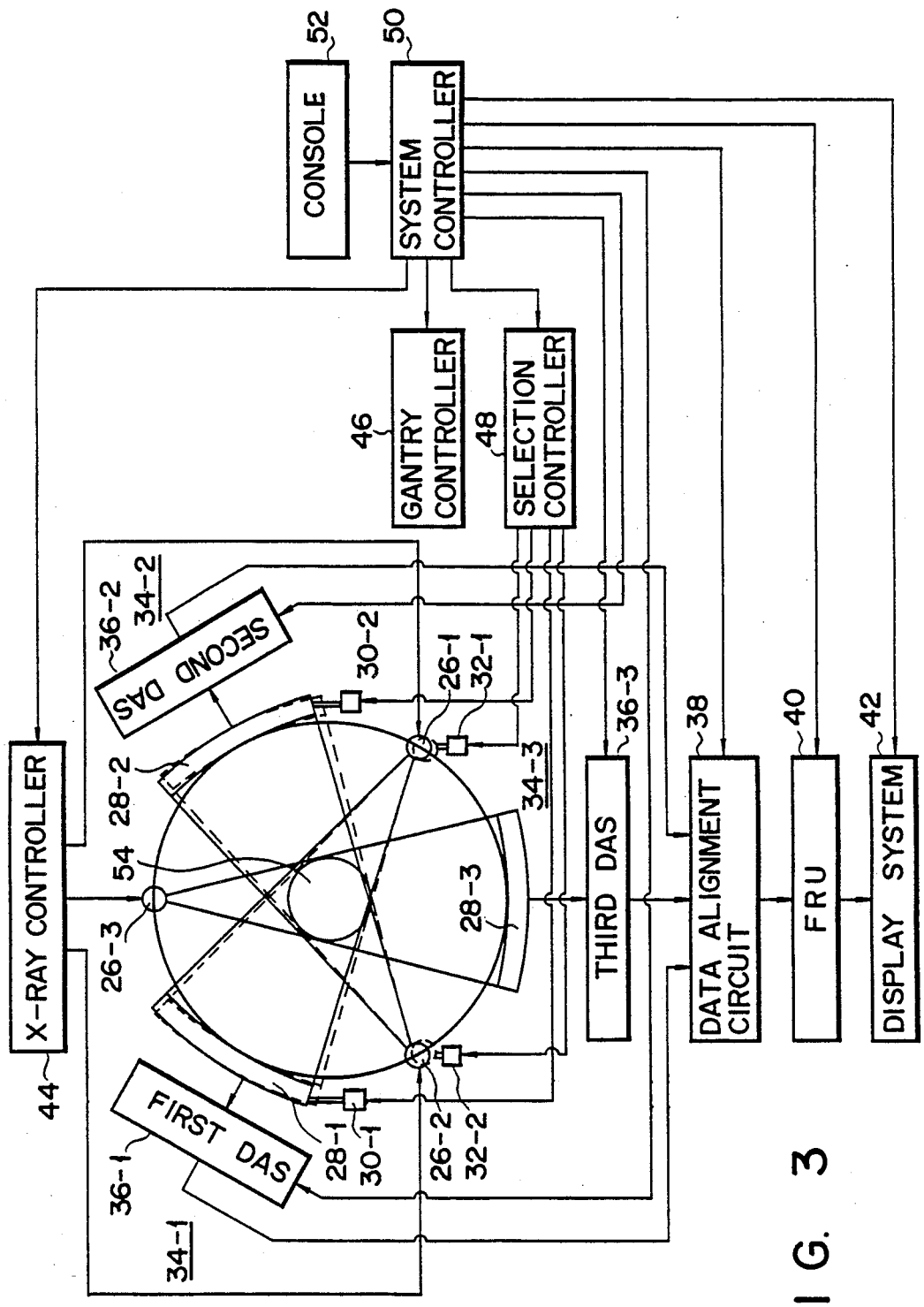

As shown in FIG. 3, the multichannel X-ray detector 28-1 of the first pair 34-1 is connected to a first DAS (data acquisition system) 36-1, the multichannel X-ray detector 28-2 of the second pair 34-2 is connected to a second DAS 36-2, and the multichannel X-ray detector 28-3 of the third pair 34-3 is connected to a third DAS 36-3. Each DAS comprises integrators, the number of which corresponds to the number of channels, a data switching multiplexer, an A/D converter, and a transfer circuit.

Data outputs of the first to third DAS's 36-1, 36-2 and 36-3 are collected to a data alignment circuit 38 and are subjected to data aligning processing.

The aligned data groups output from the data alignment circuit 38 are supplied to an FRU (fast reconstruction unit) 40 and are subjected to reconstruction processing such as filtered back projection, thus producing an image. The produced image is displayed on a display system 42.

A control system includes an X-ray controller 44, a gantry controller 46, a selection controller 48, a system controller 50, and a console 52. The system controller 50 delivers commands to the X-ray controller 44, gantry controller 46, and selection controller 48. As a result, the X-ray controller 44 supplies control signals to the X-ray sources 26-1, 26-2 and 26-3 to apply high voltage for X-ray irradiation to these X-ray sources. The gantry controller 46 controls the tilting mechanism 18, controls the motor 24 for rotating the rotational frame 26, and controls a bed (not shown). The selection controller 48 controls the shift mechanisms 30-1 and 30-2 to move the multichannel X-ray detectors 28-1 and 28-2, or controls the shift mechanisms 32-1 and 32-2 to move the X-ray sources 26-1 and 26-2.

The control of the shift mechanisms 30-1 and 30-2 and the control of the shift mechanisms 32-1 and 32-2 are not simultaneously carried out, since the asymmetrical relationship, i.e., the sampling pitch of $\frac{1}{3}$, can be attained only by either control. If both controls are carried out simultaneously, the asymmetrical relationship is cancelled. Hereinafter, a description will now be given of an example in which the multichannel X-ray detectors 28-1 and 28-2 are shifted to attain the asymmetrical relationship.

The shift mechanisms 30-1 and 30-2 for the multichannel X-ray detectors 28-1 and 28-2 move the multichannel X-ray detectors 28-1 and 28-2 from a first position to a second position. The first position is defined as follows. For example, suppose that an angle obtained by dividing a spread angle $\phi$ of the X-ray source 26-1 by the number M of channels of the corresponding multichannel X-ray detector 28-1 is represented by $\theta$ and three pairs K(3) are used. In this case, when the other X-ray sources 26-2 and 26-3 are rotated and moved to the position of the X-ray source 26-1, lines connecting the X-ray sources 26-2 and 26-3 and the centers of the channels of the corresponding X-ray detectors 28-2 and 28-3 are asymmetrically displaced from a line connecting the X-ray source 26-1 and the center of the channels of the X-ray detector 28-1 by about an integer number of times of $\theta/K(3)$. On the other hand, the second position is defined as follows. When the X-ray sources 26-2 and 26-3 are moved to the position of the X-ray source 26-1, the lines connecting the X-ray sources 26-2 and 26-3 and the centers of the channels of the corresponding X-ray detectors 28-2 and 28-3 coincide with the line connecting the X-ray source 26-1 and the center of the channels of the X-ray detector 28-1. In other words, in the first position, the sample pitch is divided to $\frac{1}{3}$, and, in the second position, the sample pitch is unchanged.

When the position of the third pair 34-3 is supposed to be a reference position, the line connecting the X-ray source 26-1 and the X-ray detector 28-1 of the first pair 34-1 is displaced from the third pair 34-3 by $+(-)\frac{1}{3} \times \theta$. Similarly, the second pair 34-2 is displaced from the third pair 34-3 by $+(-)\frac{2}{3} \times \theta$.

As described above, in this embodiment, an operator operates the console 52, so that the system controller 50, selection controller 48, and shift mechanisms 30-1 and 30-2 are controlled to set the pairs 34-1, 34-2 and 34-3 to the first position (asymmetrical position) shown in FIG. 4A, in which the sample pitch is divided to $\frac{1}{3}$, or to the second position (symmetrical position) shown in FIG. 4B, in which the sample pitch is unchanged.

As stated above, the three pairs 34-1, 34-2 and 34-3 are asymmetrically arranged with respect to the axis of rotation and are displaced from one another by $n \times \frac{1}{3} \times \theta$ (where $n = \pm 1, \pm 2$, and $\theta =$ normal sample pitch). After one rotation of the three pairs, data groups are acquired through the DAS's 36-1, 36-2 and 36-3 and are collected by the FRU 40. In this way, data rows of $\frac{1}{3}$ of the normal data pitch (sampling pitch) $\theta$ are obtained. Based on the data rows, reconstruction images are produced.

The operation of the above embodiment will now be described in greater detail. In FIG. 5A, reference numeral 56 denotes a focal point of the X-ray source, and numerals 58-1, 58-2, 58-3 and 58-4 denote X-ray paths. The position of the third pair 34-3, which is immovably arranged, is supposed to be a reference position. The sampling point of the second pair 34-2 is displaced from that of the third pair 34-3 by $-\frac{1}{3}\theta$, and the sampling point of the first pair 34-1 is displaced from that of the third pair 34-3 by $\frac{2}{3}\theta$. With this arrangement, data groups are acquired for every single rotation of the pairs.

Data obtained by the first pair 34-1 is represented by DA(n, m) (where n=0 to N, m=1 to M). In this embodiment, M=3, and n=value corresponding to the rotational position of the X-ray source 1. If 360 sampling data items are obtained in one rotation, the value of n increases by 1 at every angle of 1°. Namely, N=359.

Regarding data DB(n, m) obtained by the second pair 34-2 and data DC(n, m) obtained by the first pair 34-1, total data D obtained by one rotation is given by the following formula:

$$D(n, m') = \begin{cases} DC\left(n, \dfrac{m'}{3}\right); \text{ for } m' = 0, 3, \ldots, 3 \times M \\ DB\left(n, \dfrac{m' - 1}{3}\right); \text{ for } m' = 1, 4, \ldots, 3 \times M + 1 \\ DA\left(n, \dfrac{m' - 2}{3}\right); \text{ for } m' = 2, 5, \ldots, 3 \times M + 2 \end{cases}$$

where $m' = 0 \sim 3 \times (M+1) - 1$

In other words, the apparatus according to this embodiment can produce the same data rows as is obtained in a system wherein the number of channels of an X-ray detector in one pair is tripled and K-number of sampling operations are performed in one rotation. If the sampling pitch $\theta$ is reduced to $\frac{1}{3}\theta$, the space resolution and resolving power are improved. In FIG. 5B, solid lines 58-1, 58-2 and 58-3 indicate paths of the third pair 34-3, broken lines 60-1, 60-2 and 60-3 indicate paths of the second pair 34-2, and dot-and-dash lines 62-1, 62-2 and 62-3 indicate paths of the first pair 34-1.

When high resolution is required, one-rotation scanning is performed with the arrangement shown in FIG. 4A being employed. When high-speed scanning, rather than the high resolution, is required, $\frac{1}{3}$-rotation scanning is performed with the arrangement shown in FIG. 4B being employed.

In addition, in the state shown in FIG. 4A, by producing three data rows each obtainable by $\frac{1}{3}$ rotation, the same effect as is obtained with a triple number of channels can be attained. In this case, however, data correction corresponding to displacements between the respective pairs needs to be carried out.

FIG. 6A is a graph showing characteristics in the case of the unchanged sampling pitch, and FIG. 6B is a graph showing characteristics in the case of the one-third sampling pitch. Compared to the characteristics shown in FIG. 6A, the Nyquist frequency is tripled in FIG. 6B. Thus, even if reconstruction frequency response is extended to a high region, images free from artifact can be obtained. As a result, the value of MTF of image, that is, a product of the value of the frequency response in an image reconstruction system and the value of the frequency response in an X-ray beam system, can be extended to a high frequency region.

In the above example, in order to attain the asymmetrical relationship, the shift mechanisms 30-1 and 30-2 are operated to move the multichannel X-ray detectors 26-1 and 26-2. It is, however, possible to operate the shift mechanism 32-1 and 32-2 to move the X-ray sources 28-1 and 28-2 while the multichannel X-ray detectors 26-1 and 26-2 are kept in the symmetrical position. In other words, in the apparatus shown in FIGS. 1 to 3, the asymmetrical relationship between each pair can be attained by the method in which the multichannel X-ray detectors 26-1 and 26-2 while the X-ray sources 28-1 and 28-2 are kept in the symmetrical position, or by the method in which the X-ray sources 28-1 and 28-2 are moved while the multichannel X-ray detectors 26-1 and 26-2 are kept in the symmetrical position.

In the apparatus of the above example, the same advantage can be obtained by the two methods. However, the structure of the apparatus may be made simpler, if the apparatus designed to use only one of the two methods.

Figure 7:
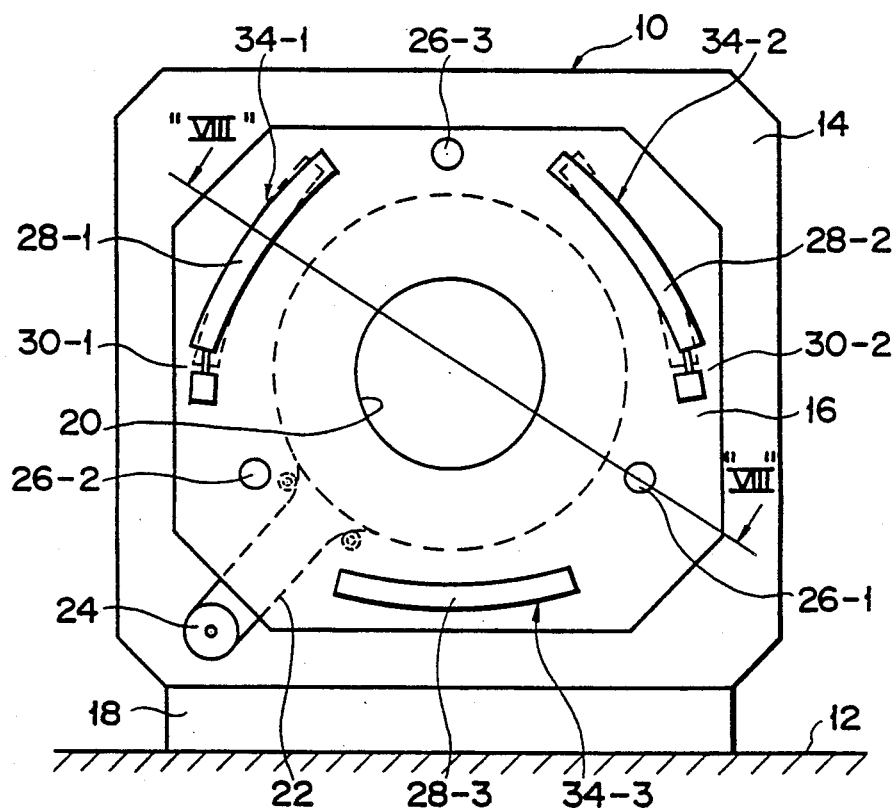
Figure 8:
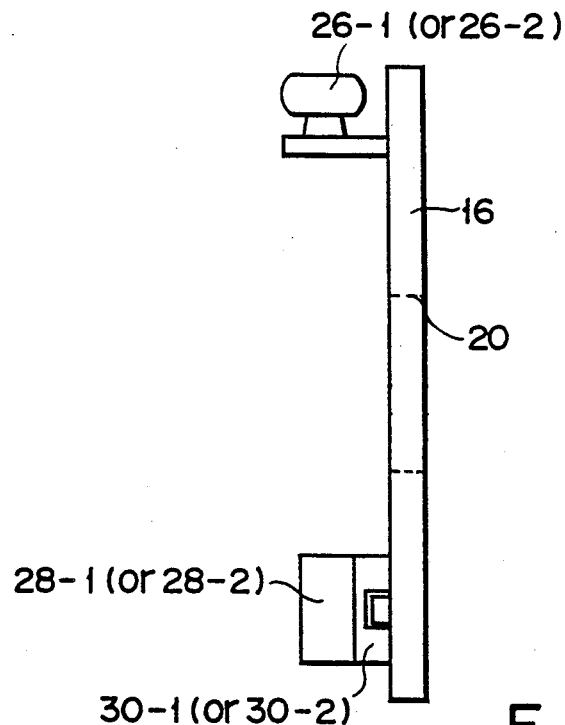
Figure 9:
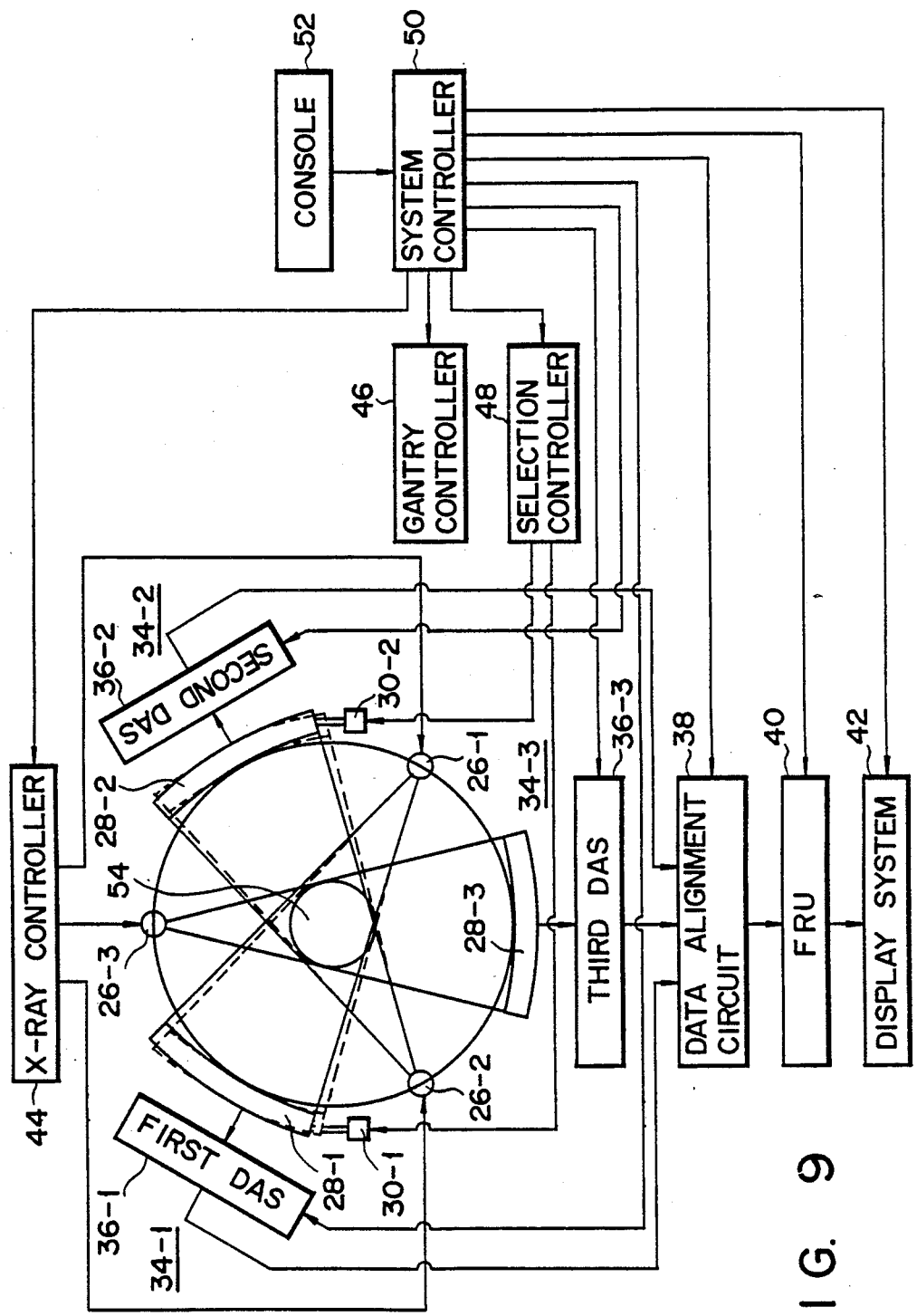

FIGS. 7 to 9 show a rotate-rotate type X-ray computerized tomographic imaging apparatus according to a second embodiment of the invention, which has this type of arrangement. FIG. 7, which corresponds to FIG. 1 showing the first embodiment, is a front view of a gantry. FIG. 8, which corresponds to FIG. 2 showing the first embodiment, is a cross section of a rotational body taken along line VIII—VIII in FIG. 7. FIG. 9, which corresponds to FIG. 3 showing the first embodiment, is a block diagram of an electric circuit.

In the above embodiments, three pairs have been employed. However, the number of pairs is not limited to three if the following condition is met. Namely, in the case where K-number of pairs are used and an angle obtained by dividing a spread angle $\phi$ of an X-ray source of a given pair by the number M of channels of the corresponding multichannel X-ray detector is represented by $\theta$, when other X-ray sources are rotated and moved to the position of the X-ray source of the given pair, lines connecting the other X-ray sources and the centers of the channels of the corresponding X-ray detectors are displaced asymmetrically from a line connecting the X-ray source of the given pair and the center of the channels of the corresponding X-ray detector by about an integer number of times of $\theta/K$.

Other modifications and changes may be made to the present invention within the spirit of the subject matter of the present invention.

As described above, in the present invention, a plurality of pairs of X-ray sources and X-ray detectors are used, and these pairs are arranged asymmetrically with respect to the axis of rotation of the rotational frame. When data groups of different pairs obtained after one rotation of the frame are aligned, data having a smaller data pitch than the pitch used in a conventional one-pair type apparatus can be produced. As a result, an image having high space resolution can be obtained. In addition, even if the rotational frame is not rotated over 360°, projection data groups similar to those obtained by a single-pair construction can be produced. Based on these data groups, reconstruction of images is carried out, and the scanning speed is increased, and the scanning time is shortened.

The present invention can provide a rotate-rotate type X-ray computerized tomographic imaging apparatus having high scanning speed and high space resolving power.

What is claimed is:

1. A rotate-rotate type x-ray computerized tomographic imaging apparatus comprising:
    a stationary body;
    a rotational body arranged to rotate in said stationary body about an axis of rotation and having an insertion section in which a subject is inserted;
    K x-ray sources arranged on said rotating body around said axis of rotation, where K is an integer greater than 1;
    K multi-channel x-ray detectors arranged on said rotating body around said axis of rotation with each detector located opposite a corresponding source to form K source/detector pairs, with K−1 of said pairs adjustable between a symmetric condition in which said K pairs are angularly oriented symmetrically about said axis of rotation such that a first sample pitch of data is obtainable and an asymmetric condition in which said K−1 pairs are angularly oriented asymmetrically with respect to said axis of rotation such that a second sample pitch of data 1K of said first sample pitch of data is obtainable;
    data processor means for collecting data from said K detectors and for processing image reconstruction from that data; and
    controller means for controlling rotation of said body, data collection, and image reconstruction.

2. The apparatus of claim 1 wherein said controller means includes a high resolution scan mode and a short time scan mode, said high resolution scan mode including control of said K−1 pairs to place said K−1 pairs in said asymmetric condition and control of said rotating body to rotate said rotating body at least by a single complete rotation to obtain a single image, and said short time scan mode including control of said K−1 pairs to place said K pairs in said symmetric condition and control of said rotating body to rotate said rotating body at least by 1/K of a single complete rotation to obtain a single image.

3. In a rotate-rotate type x-ray computerized tomographic imaging apparatus, comprising:
    a stationary body;
    a rotational body arranged to rotate in said stationary body about an axis of rotation and having an insertion section in which a subject is inserted;
    K x-ray sources arranged to said rotating body, where K is an integer greater than 1;
    K multichannel x-ray detectors arranged to said rotating body, with each of said sources arranged opposite a corresponding detector to provide K source/detector pairs and with said pairs arranged around said axis of rotation of said rotational body;
    data processor means for collecting data from said detectors and for processing image reconstruction from that data;
    the improvement comprising:
    means for shifting the relative angular positions of K−1 of said pairs; and
    control means for controlling rotation of said body, data collection, and image reconstruction, said control means having a short time scan mode and a high resolution scan mode,
    said short time scan mode including control of said means for shifting to angularly orient said K pairs symmetrically with respect to said axis of rotation such that a first sample pitch of data is obtainable and control of said rotational body to rotate said rotational body at least 1/K of a single complete rotation to obtain a single image, and
    said high resolution scan mode including control of said means for shifting to angularly orient said K−1 pairs asymmetrically with respect to said axis of rotation such that a second sample pitch of data 1K of said first sample pitch of data is obtainable and control of said rotational body to rotate said rotational body at least a single complete rotation to obtain a single image.

4. The apparatus of claim 3 wherein said means for shifting comprises means for selectively positioning the sources corresponding to said K−1 pairs to permit said control means to make focus points of said sources shift slightly on the corresponding detectors.

5. The apparatus of claim 3 wherein said means for shifting comprises means for selectively positioning the detectors corresponding to said K−1 pairs to permit said control means to make focus points of said sources shift slightly on the corresponding detectors.

* * * * *

UNITED STATES PATENT AND TRADEMARK OFFICE
CERTIFICATE OF CORRECTION

PATENT NO. : 4,991,190
DATED : February 05, 1991
INVENTOR(S) : Issei Mori

It is certified that error appears in the above-identified patent and that said Letters Patent is hereby corrected as shown below:

Claim 1, column 7, line 49, change "1K" to --1/K--.

Claim 3, column 8, line 16, change "arranged" to --attached--.

Claim 3, column 8, line 18, change "arranged" to --attached--.

Claim 3, column 8, line 44, change "1K" to --1/K--.

Signed and Sealed this

Sixth Day of April, 1993

Attest:

STEPHEN G. KUNIN

*Attesting Officer*     *Acting Commissioner of Patents and Trademarks*